(12) United States Patent
Phillips

(10) Patent No.: US 6,217,504 B1
(45) Date of Patent: Apr. 17, 2001

(54) RESILIENT FILLED-BLADDER MAGNETHERAPY ARTICLES

(75) Inventor: Lester Phillips, Houston, TX (US)

(73) Assignee: Gayla Industries, Inc., Houston, TX (US)

(*) Notice: Subject to any disclaimer, the term of this patent is extended or adjusted under 35 U.S.C. 154(b) by 0 days.

(21) Appl. No.: 09/310,709

(22) Filed: May 12, 1999

(51) Int. Cl.⁷ .............................. A61B 17/52; A61N 2/00
(52) U.S. Cl. ................................................. 600/9
(58) Field of Search ..................... 600/9, 15, 13, 600/10, 14; 601/118, 19, 135; 482/49; 446/267; 248/118

(56) References Cited

U.S. PATENT DOCUMENTS

| | | | | |
|---|---|---|---|---|
| 4,489,711 | * | 12/1984 | Latzke | 600/15 |
| 4,952,190 | * | 8/1990 | Tarnoff | 446/267 |
| 5,137,507 | * | 8/1992 | Park | 600/13 |
| 5,139,014 | * | 8/1992 | Chang | 601/118 |
| 5,143,056 | * | 9/1992 | Yih-Jong | 601/118 |
| 5,158,255 | * | 10/1992 | Fuller | 248/118 |
| 5,161,272 | * | 11/1992 | Yamaguchi et al. | 600/9 |
| 5,228,655 | * | 7/1993 | Garcia et al. | 248/118 |
| 5,350,342 | * | 9/1994 | Scatterday | 482/49 |
| 5,389,063 | * | 2/1995 | Wu | 601/135 |
| 5,445,349 | * | 8/1995 | Hart | 248/118 |
| 5,566,913 | * | 10/1996 | Prokop | 248/118 |
| 5,575,760 | * | 11/1996 | Masuda | 601/19 |
| 5,718,655 | * | 2/1998 | Phillips | 482/49 |
| 5,738,624 | * | 4/1998 | Zablotsky et al. | 600/9 |
| 5,782,743 | * | 7/1998 | Russel | 600/9 |
| 5,839,992 | * | 11/1998 | Phillips | 482/49 |

* cited by examiner

*Primary Examiner*—Max Hindenburg
*Assistant Examiner*—Brian Szmal
(74) *Attorney, Agent, or Firm*—Kenneth A. Roddy

(57) ABSTRACT

Resilient magnetherapy articles having a powder-like filler material including magnetic elements contained within a resilient bladder are disclosed for exercising the muscles of the wrist, hand, fingers and forearm of the user, and for supporting the wrist of a person performing repetitive tasks with their wrist, hand and fingers, such as using a computer mouse and typing on a keyboard, while at the same time providing the beneficial effect of magnetic therapy. A mass of tiny glass spheres having the consistency and appearance of a fine powder is enclosed in a resilient inner bladder surrounded by a resilient outer bladder and a thin layer of lubricating powder is disposed between the exterior surface of the inner bladder and interior surface of the outer bladder to prevent them from sticking together, reduce friction therebetween, and allow relative sliding movement between the surfaces when squeezed in the palm of the hand. The tiny spheres provide low resistance to relative particle movement by rolling on each other upon an increase or decrease in applied pressure. When placed on a flat surface beneath the wrist of a user, the article deforms slightly and conforms to the underside of the user's wrist to form a comfortable cradle-like support as the downward pressure of the wrist increases or decreases. As the wrist is moved relative to the flat surface, the article smoothly rolls between the wrist and the flat surface to provide a smooth massaging effect on the wrist while maintaining wrist support.

11 Claims, 2 Drawing Sheets

RESILIENT FILLED-BLADDER MAGNETHERAPY ARTICLES

BACKGROUND OF THE INVENTION

1. Field of the Invention

This invention relates generally to magnetherapy and exercise devices, and more particularly to resilient filled-bladder magnetherapy articles for exercising the hand and fingers of the user and supporting the wrist of a user to provide beneficial magnetic effects while exercising the hand and fingers and performing repetitive tasks with their wrist, hand and fingers.

2. Brief Description of the Prior Art

Magnetic therapy is becoming an increasingly popular treatment for healing and pain reduction. It has been shown in clinical tests that a magnetic field possess circulation-enhancing properties, which results in more oxygen and nutrients delivered to the cells, removal of metabolic by-products from the blood, helps promote pH balance, and may reduce stiffness, pain and inflammation.

Magnetic therapy devices utilizing permanent magnets are known in the art. Most magnetic therapy devices are merely worn on the person's body, or contain rigid magnets applied to the person's body in a massaging action, and do not provide the beneficial effect of muscular exercise.

Park, U.S. Pat. No. 5,137,507 discloses a magnetic ring made of multi-angled and coiled string which is encircled around and rolled up and down on a finger or toe or rubbed against the toes.

Chang, U.S. Pat. No. 5,139,014, Yih-Jong, U.S. Pat. No. 5,143,056, and Masuda, U.S. Pat. No. 5,575,760 disclose massage devices with a plurality of stiff magnets contained in protuberances on their outer surface.

Yamaguchi et al, U.S. Pat. No. 5,161,272 discloses a mattress having protuberences on its surface and a damper felt layer dotted with permanent magnets.

Zablotsky et al, U.S. Pat. No. 5,738,624 discloses a face mask made of flexible sheets of plastic material having a layer of viscous material or deformable thermoplastic material therebetween and provided with permanent magnet sheet elements which overlie forehead, temple, cheek, and mouth areas of the face.

Russell, U.S. Pat. No. 5,782,743 discloses a band or belt which is worn around a to-be-treated portion of a user's body and one or magnetizable stainless steel C-shaped clips each containing a permanent that are adjustably position on the band or belt.

Wu, U.S. Pat. No. 5,389,063 disclose a rigid massaging ball structure having a magnetic rod in the center surrounded by arch-shaped rails having a plurality of massaging elements engaged thereon with protrusions on the outer surface of the massaging elements.

Other therapeutic hand exercisers are also known in the art which fit into the palm of the hand, however they do not provide magnetic properties.

A resilient rubber hand exerciser known as the "Eggserciser" (TM) is sold by Eggstra Enterprises, Inc., of Alabaster, Ala. This device is an egg-shaped member molded of homogeneous foam rubber.

A pliable hand exerciser sold by Qualatex of Wichita, Kansas under the name "Ad Impressions" (TM) ASI 78200 is a natural latex balloon filled with hard granular particles.

Therapeutic hand exercisers known as the "Gripp" (TM) and "Thera-Gripp" (TM) are sold by Abilitations of Atlanta Ga. These devices are filled with a grain material.

Scatterday, U.S. Pat. No. 5,350,342 discloses a deformable semi-resilient grip having a filler material which includes a mixture of lubricating powder and particles.

Tarnoff, U.S. Pat. No. 4,952,190 discloses a deformable novelty toy containing a cohesive mixture of low-density microspheres and a small amount of liquid, such as water, mineral oils, glycols, etc., in an amount effective to unite the microspheres and provide cohesion and moldability.

Wrist support devices for supporting the wrist of a person performing repetitive tasks with their wrist, hand and fingers, such as using a computer mouse and typing on a keyboard are also known in the art.

There are several commercially available wrist support devices which consist of a pad formed of neoprene or homogeneous foam rubber that may be attached to a computer mouse or keyboard. These types of wrist supports are relatively stiff and non-compliant to the user's wrist. Other wrist support devices are known which utilize an outer covering or bladder filled with a gel, or with seed, grain, or other "granular" or crystalized particles.

Garcia et al, U.S. Pat. No. 5,228,655 discloses a wrist rest support which includes a base pad that is positioned partially under the keyboard or mouse and a section extending away therefrom that has a top surface for supporting the wrists. Prokop, U.S. Pat. No. 5,566,913 discloses a wrist rest apparatus which includes an elastic envelope filled with a gelatinous material that supports the wrist and may also be heated or cooled to provide additional therapeutic effects. In some embodiments, the Hart device can be grasped with both hands and squeezed to function as an exercise means.

Hart, U.S. Pat. No. 5,445,349 discloses a wrist support system which includes an elongate cloth container and particulate material such as rice disposed within the interior of a tubular-shaped segment. The device provides a stable support for the wrist and gently massages the wrist during finger movement, and may also be heated or cooled to provide additional therapeutic effects.

Fuller, U.S. Pat. No. 5,158,255 discloses a generally cylindrical wrist rest apparatus which includes a tubular solid rigid core surrounded by a yieldable foam layer having an irregular exterior and a soft fabric outer covering. The device provides a support for the wrist and can also be grasped and squeezed to function as an exercise means.

My prior U.S. Pat. Nos. 5,718,655 and 5,839,992, commonly owned with this application, and hereby incorporated herein by reference, disclose resilient therapeutic hand exercisers and wrist supports containing a mass of tiny glass spheres having the consistency and appearance of a fine powder enclosed in a resilient double bladder, but do not have any magnetic properties.

The present invention is distinguished over the prior art in general, and these patents in particular, by resilient magnetherapy articles having a powder-like filler material including magnetic elements contained within a resilient bladder for exercising the muscles of the wrist, hand, fingers and forearm of the user, and for supporting the wrist of a person performing repetitive tasks with their wrist, hand and fingers, such as using a computer mouse and typing on a keyboard, while at the same time providing the beneficial effect of magnetic therapy. A mass of tiny glass spheres having the consistency and appearance of a fine powder is enclosed in a resilient inner bladder surrounded by a resilient outer bladder and a thin layer of lubricating powder is disposed between the exterior surface of the inner bladder and interior surface of the outer bladder to prevent them from sticking together, reduce friction therebetween, and allow relative sliding movement between the surfaces when squeezed in the palm of the hand. The tiny spheres provide low resistance to relative particle movement by rolling on each other upon an increase or decrease in applied pressure. When placed on a flat surface beneath the wrist of a user, the article deforms slightly and conforms to the underside of the user's wrist to form a comfortable cradle-like support as the downward pressure of the wrist increases or decreases. As the wrist is moved relative to the flat surface, the article smoothly rolls between the wrist and the flat surface to provide a smooth massaging effect on the wrist while maintaining wrist support.

SUMMARY OF THE INVENTION

It is therefore an object of the present invention to provide a resilient filled-bladder magnetherapy hand exerciser article that produces a magnetic field and can be squeezed in the palm of the hand to provide the user with simultaneous magnetic therapy effects and muscular exercise.

It is another object of this invention to provide a resilient filled-bladder magnetherapy wrist support article that produces a magnetic field and comfortably supports the wrist of a user to simultaneously provide the user with magnetic therapy effects while performing repetitive tasks with their wrist, hand and fingers, such as using a computer mouse and typing on a keyboard.

Another object of this invention is to provide a combination resilient filled-bladder magnetherapy hand exercise and wrist support article that produces a magnetic field and can be placed adjacent to a computer mouse or keyboard for supporting the wrist of the user and can also be squeezed in the palm of the hand for use as a therapeutic resilient hand exerciser, while providing magnetic therapy effects during such use.

Another object of this invention is to provide resilient filled-bladder magnetherapy hand exerciser and wrist support articles having a double wall bladder of resilient material with a lubricating talc powder layer between the double plies of resilient material to provide resiliency, flexibility, compressibility, and strength without excessive wall thickness.

A further object of this invention is to provide resilient filled-bladder magnetherapy hand exerciser and wrist support articles having a double wall bladder of resilient material with a lubricating talc powder layer between the double plies of resilient material to prevent the double plies of material from sticking together and allow the plies of resilient material to slide relative to one another when the article is compressed, thus reducing wear and friction between the plies and extending the life of the product.

A still further object of this invention is to provide resilient filled-bladder magnetherapy hand exerciser and wrist support articles having a resilient bladder containing a mass of tiny glass spheres having the consistency of a fine powder with magnetic elements disposed therein wherein the tiny spheres roll on each other as the article is squeezed and the pressure is released and thereby providing low resistance to relative movement of the filler material and allowing the article to be compressed quickly and to resume its natural shape quickly.

Other objects of the invention will become apparent from time to time throughout the specification and claims as hereinafter related.

The above noted objects and other objects of the invention are accomplished by resilient magnetherapy articles having a powder-like filler material including magnetic elements contained within a resilient bladder for exercising the muscles of the wrist, hand, fingers and forearm of the user, and for supporting the wrist of a person performing repetitive tasks with their wrist, hand and fingers, such as using a computer mouse and typing on a keyboard, while at the same time providing the beneficial effect of magnetic therapy. A mass of tiny glass spheres having the consistency and appearance of a fine powder is enclosed in a resilient inner bladder surrounded by a resilient outer bladder and a thin layer of lubricating powder is disposed between the exterior surface of the inner bladder and interior surface of the outer bladder to prevent them from sticking together, reduce friction therebetween, and allow relative sliding movement between the surfaces when squeezed in the palm of the hand. The tiny spheres provide low resistance to relative particle movement by rolling on each other upon an increase or decrease in applied pressure. When placed on a flat surface beneath the wrist of a user, the article deforms slightly and conforms to the underside of the user's wrist to form a comfortable cradle-like support as the downward pressure of the wrist increases or decreases. As the wrist is moved relative to the flat surface, the article smoothly rolls between the wrist and the flat surface to provide a smooth massaging effect on the wrist while maintaining wrist support.

DESCRIPTION OF THE PREFERRED EMBODIMENT

Figure 1:
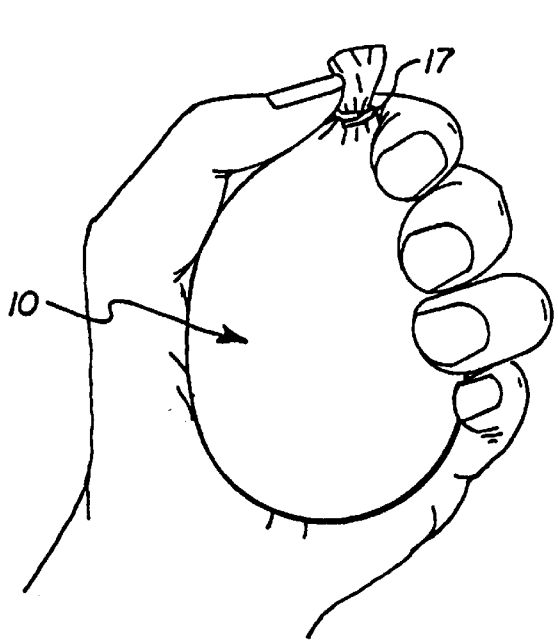
FIG. 1 is a perspective view of a resilient filled-bladder magnetherapy hand exercise article in accordance with the present invention being squeezed in the palm of a hand.
Figure 2:
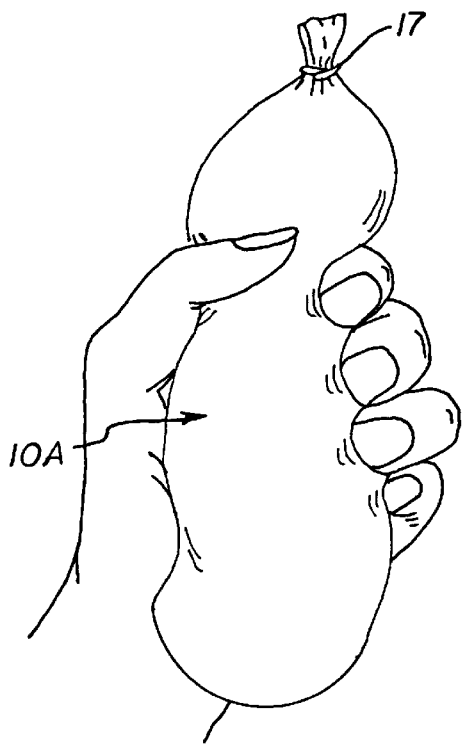
FIG. 2 is a perspective view of a combination resilient filled-bladder magnetherapy hand exercise and wrist support article in accordance with the present invention being squeezed in the palm of the hand.
Figure 3:
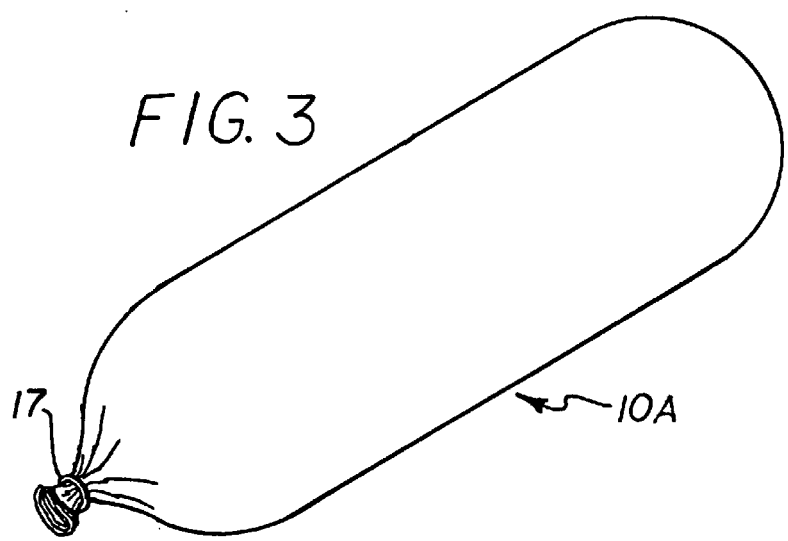
FIG. 3 is a perspective view of the combination resilient filled-bladder magnetherapy wrist support and therapeutic hand exercise article of FIG. 2.

Referring to the drawings by numerals of reference, there is shown in FIG. 1, a preferred resilient filled-bladder magnetherapy hand exerciser 10 in accordance with the present invention, and in FIGS. 2 and 3, a preferred combination resilient filled-bladder magnetherapy hand exerciser and wrist support 10A in accordance with the present invention.

In its natural state, the resilient filled-bladder magnetherapy hand exerciser 10 is a generally oval-shaped article having a diameter of approximately 2¼" and a length of approximately 2½" to fit into the palm of the hand of the user. As shown in FIGS. 2 and 3, the combination resilient filled-bladder magnetherapy hand exerciser and wrist support 10A, in its natural state, is a generally cylindrical-shaped article approximately 2¼" in diameter and approximately 6" in length. Except for their length, the articles 10 and 10A are of the same construction.

Figure 4:
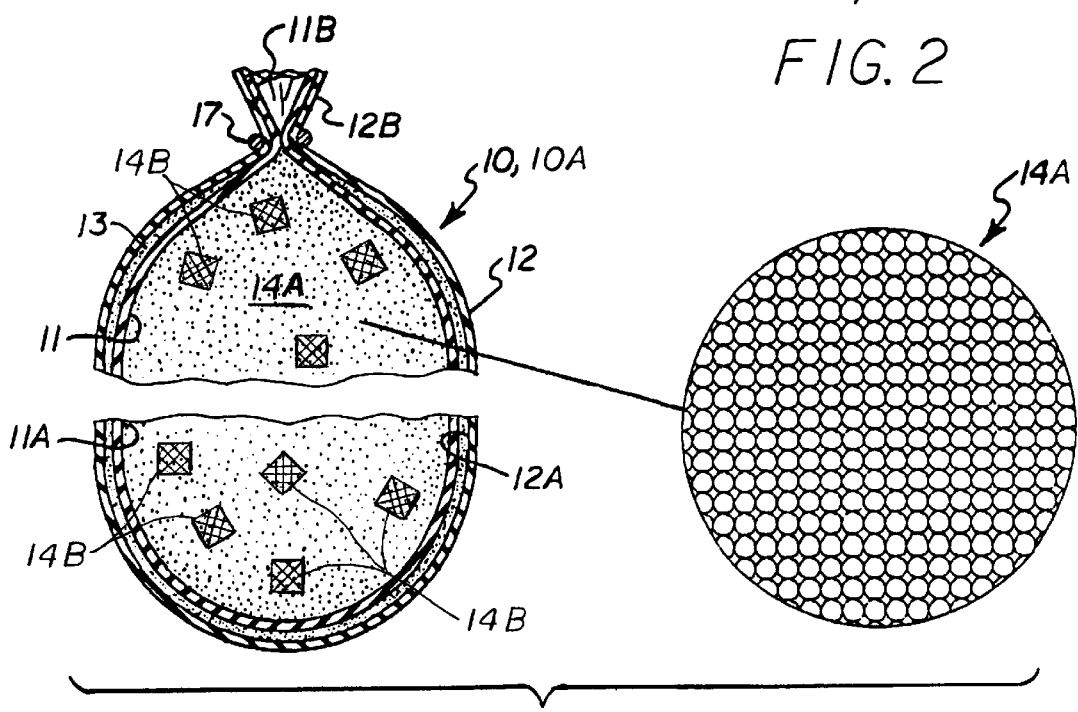
FIG. 4 is a cross section view showing the interior of the resilient filled-bladder magnetherapy articles.

FIG. 4 shows, in cross section, the interior of the resilient filled-bladder magnetherapy articles 10 and 10A. The articles 10 and 10A are formed of an inner bladder 11 and an outer bladder 12 formed of resilient material such as latex rubber. Each bladder 11 and 12 has a main body portion 11A and 12A and a tubular neck portion 11B and 12B, respectively.

The inner and outer bladders 11 and 12 are superposed to provide a double layer of resilient material. A thin layer or coating of lubricating talc powder 13 is disposed between the exterior of the main body portion 11A and the interior of the main body portion 12A, to prevent friction or sticking between the superposed layers and allow relative movement therebetween.

The interior of the inner resilient bladder 11 is filled with a powder-like material 14A and a plurality small magnetic elements 14B. In a preferred embodiment, the powder-like material 14A is formed of tiny glass spheres having a particle size ranging from about 70 to about 140 mesh (U.S. standard), which equates to a particle diameter of from about 0.0083" to about 0.0041". The filler material 14A is represented schematically in the drawing figure. In reality, the filler material has the consistency and appearance of a fine white powder. The tiny glass sphere material 14A has a density of about 98 lbs/ft. The tiny glass spheres are formed of soda-lime glass, or glass oxide. A suitable glass sphere material is manufactured by Potters Industries Inc., of Carlstadt, N.J. and known commercially as "Impact Beads".

The preferred magnetic elements 14B are formed of commercially available flexible unipole magnetic sheet material, that is cut into small squares approximately ¼"×¼" and 1/16" thick. Approximately 6–10 squares 14B are used in the bulbous embodiment of FIG. 1 and approximately 6–20 squares are used in the elongate cylindrical embodiment of FIGS. 2 and 3. The magnetic material has a Gauss rating in the range of from about 500 to about 3500, and preferrably about 2200 to 2500.

The open end of the bladders 11 and 12 is sealed by securing a wire staple 17 around the superposed neck portions 11B and 12B. The wire staple 17 does not penetrate the resilient material, but is crimped around the neck portions 11B and 12B in the manner of a sausage staple on a sausage casing.

As shown in FIGS. 1 and 2, the articles 10 and 10A may be used as a therapeutic hand exerciser. The article 10 or 10A is placed in the palm area of the hand and is squeezed and released for exercise and therapy of the muscles of the wrist, hand, fingers, and forearm. The articles 10 and 10A provide a smooth resilient resistance to the squeezing pressure, while at the same time provide the additional beneficial effect of magnetic therapy.

The double bladders 11 and 12 provide a resilient double ply exterior wall which gives the article resiliency, flexibility, compressibility, and strength without excessive wall thickness. The layer of lubricating talc powder 13 between the double ply walls prevents the plies of resilient material from sticking together and allows the plies to slide relative to one another when the article is squeezed and released. This feature prevents wear or friction between the bladder walls and extends the life of the product.

The tiny glass spheres forming the powder-like filler material 14A roll on each other as the article is squeezed and the pressure is released. Thus, the filler material 14A of the present invention has a low resistance to relative movement. This feature allows the article to be compressed quickly and to resume its natural shape quickly when the resiliency of the double wall bladder forces the article to resume its natural shape.

The combination of the resilient double ply wall with the lubricating talc powder layer between the double ply walls and the powder-like tiny glass spheres which roll on each other as the article is squeezed and released give the present invention a unique smooth "squishy" feeling when squeezed and released, and makes it more resiliently responsive than prior art hand exercisers filled with sand, seed, grain, or other "granular" or crystalized material which have flat surfaces and/or sharp points.

The magnetic elements 14A create a magnetic field that penetrates the tissues of the hand. It is known that a magnetic field possess circulation-enhancing properties, which results in more oxygen and nutrients delivered to the cells, removal of metabolic by-products from the blood, helps promote pH balance, and may reduce stiffness, pain and inflammation. Thus, the user is exposed to the beneficial effects of the magnetic field, while at the same time flexing the muscles, tendons and joints of the hand that are exposed to the magnetic field.

Unlike prior art magnetherapy devices such as belts, face masks, and shoe inserts, which are merely worn or placed against the body, the present invention has the additional therapeutic benefit of providing resistive muscular exercise to the muscles, tendons and joints.

Figure 5:
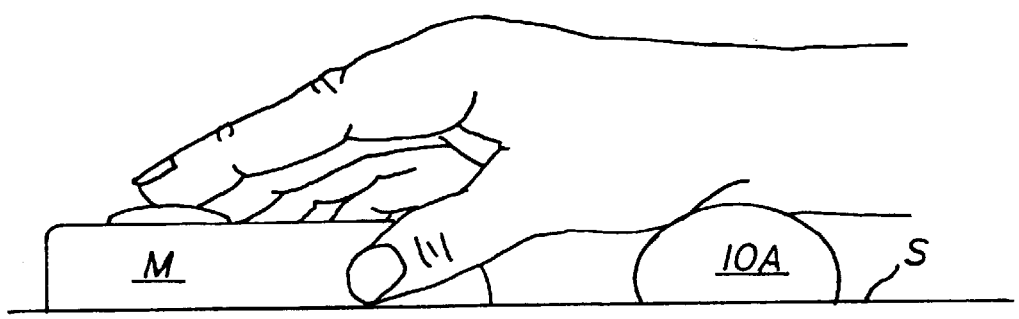
FIG. 5 is a side elevation showing the combination resilient filled-bladder magnetherapy wrist support and therapeutic hand exerciser of FIGS. 2 and 3 being used to support the wrist of a person using a computer mouse.
Figure 6:
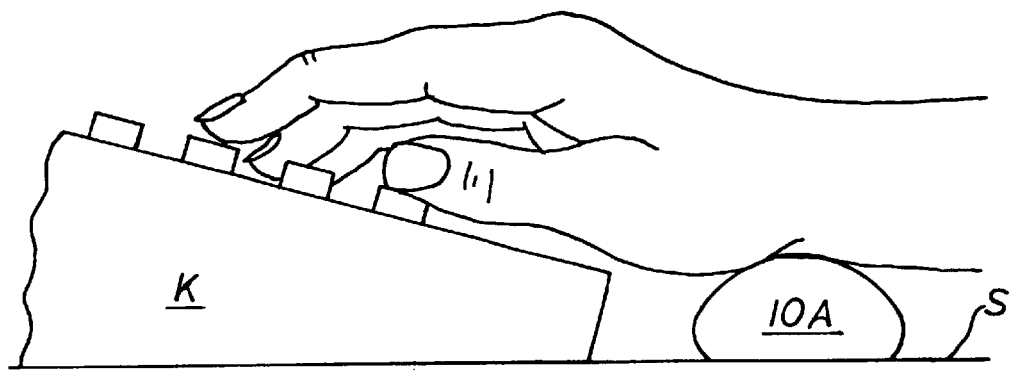
FIG. 6 is a side elevation showing the combination resilient filled-bladder magnetherapy wrist support and therapeutic hand exerciser of FIGS. 2 and 3 being used to support the wrist of a person using a keyboard.

As shown in FIGS. 5 and 6, the combination resilient filled-bladder magnetherapy hand exerciser and wrist support 10A may also be used as a wrist support. The article 10A is placed onto a flat surface S adjacent to a computer mouse M or keyboard K. The user then places the underside of their wrist on the top surface of the article. The user may reposition the article to so as to provide a comfortable support for the wrist, and the weight of the user's wrist causes the article to deform slightly such that the underside of the article flattens against the flat surface S and its top side conforms to the shape of the underside of the wrist and thereby forms a comfortable supporting cradle for the wrist while using the mouse or keyboard, and at the same time the user is exposed to the beneficial effects of the magnetic field.

The user may also increase and decrease downward pressure of the wrist and the resiliency of the double bladder allows the article to maintain engagement with the wrist and apply a resistive upward pressure. The wrist may also be moved forward and backward over the article 10A so that it rolls between the wrist and the flat surface, and the article will maintain the cradle-like supporting engagement with the underside of the wrist. Thus, the smooth rolling action during wrist movement provides the wrist of the user with a soft massaging effect as the article 10A rolls between the wrist and the flat surface while exposed to the magnetic field.

While this invention has been described fully and completely with special emphasis upon a preferred embodiment, it should be understood that within the scope of the appended claims the invention may be practiced otherwise than as specifically described herein.

What is claimed is:

1. A resilient filled-bladder magnetherapy article sized and shaped to be held in the palm of a user's hand to be deformed when squeezed and resume its natural shape when squeezing pressure is relieved, comprising:

a resilient bladder formed of resilient material;

a mass of filler material having the consistency and appearance of fine powder contained within said bladder; and a plurality of magnetic elements in said mass of filler material of sufficient strength to produce a magnetic field; wherein said bladder when filled is sized and shaped to be held in the palm of a user's hand; and the resiliency of said bladder and consistency of said filler material contained therein are sufficient to allow said article to be deformed quickly against resilient resistive pressure when squeezed in the palm of the hand and to resume its natural shape quickly when squeezing pressure is relieved to exercise muscles tendons, and joints of the hand of the user while exposed to the magnetic field of said magnetic elements.

2. The magnetherapy article according to claim 1, wherein said magnetic elements comprise a plurality of flexible permanent magnets.

3. The magnetherapy article according to claim 1, wherein said magnetic elements have a Gauss rating in the range of from about 500 to about 3500.

4. The magnetherapy article according to claim 1, wherein said magnetic elements have a Gauss rating in the range of from about 2200 to about 2500.

5. The magnetherapy article according to claim 1, wherein said resilient bladder comprises an inner bladder formed of resilient material and an outer bladder formed of resilient material superposed on said inner bladder to form two plies of resilient material surrounding said mass of filler material and magnetic elements.

6. The magnetherapy article according to claim 5, further comprising a thin layer of lubricating powder disposed between an exterior surface of said inner bladder and an interior surface of said outer bladder to prevent said surfaces from sticking together, to reduce friction therebetween, and allow relative sliding movement between said inner and outer bladder surfaces.

7. The magnetherapy article according to claim 5, wherein said inner bladder and said outer bladder are formed of latex.

8. The magnetherapy article according to claim 1, wherein said mass of filler material comprises a mass of tiny glass spheres formed of glass oxide (soda-lime glass).

9. The magnetherapy article according to claim 1, wherein said mass of filler material comprises a mass of tiny spheres contained within said bladder having a particle size of from about 70 to about 140 U.S. standard mesh (about 0.0083" dia. to about 0.0041" dia.) and having the consistency and appearance of fine powder, said tiny spheres providing low resistance to relative particle movement by rolling on each other upon an increase or decrease in pressure applied to said article.

10. The magnetherapy article according to claim 9, wherein said mass of tiny spheres has a density of about 98 lbs/ft$^3$.

11. A resilient filled bladder magnetherapy article sized and shaped to be gripped and squeezed by the hand of a user to serve as a hand exerciser and also to support the wrist of a user when placed on a flat surface to serve as a wrist support, comprising:

a resilient bladder formed of resilient material;

a mass of filler material having the consistency and appearance of fine powder contained within said bladder; and a plurality of magnetic elements in said mass of filler material of sufficient strength to produce a magnetic field; wherein said bladder when filled is sized and shaped to be held in the palm of a user's hand and to support the wrist of a user when placed on a flat surface; and the resiliency of said bladder and consistency of said filler material contained therein are sufficient to allow said article to be deformed quickly against resilient resistive pressure when squeezed in the palm of the hand and to resume its natural shape quickly when squeezing pressure is relieved to exercise muscles, tendons, and joints of the hand of the user while exposed to the magnetic field of said magnetic elements; and to allow said article to be deformed slightly when placed on a flat surface beneath the user's wrist with the weight of the user's wrist causing one side of said article to flatten against the flat surface and an opposed side to engage and conform to the shape of the underside of the user's wrist to form a comfortable cradle-like support; and as the user's wrist is moved relative to the flat surface, to smoothly roll between the user's wrist and the flat surface to provide a smooth massaging effect on the wrist while exposed to the magnetic field of said magnetic elements and while the user is performing repetitive tasks with their wrist, hand and fingers, such as using a computer mouse and typing on a keyboard.

* * * * *